United States Patent [19]
Abell

[11] Patent Number: 4,874,363
[45] Date of Patent: Oct. 17, 1989

[54] COLON HYDROTHERAPY AND EVACUATOR SYSTEM

[76] Inventor: Walter L. Abell, 2773 Spaulding Dr., Dunwoody, Ga. 30338

[21] Appl. No.: 77,734

[22] Filed: Jul. 23, 1987

Related U.S. Application Data

[63] Continuation-in-part of Ser. No. 889,228, Jul. 25, 1986, abandoned.

[51] Int. Cl.4 ............................................. A61M 1/00
[52] U.S. Cl. ...................................... 604/28; 604/31; 604/34; 604/43; 604/276
[58] Field of Search .................................. 604/27–34, 604/36, 39, 41, 43, 118, 246, 247, 248, 249, 250, 275, 276, 277, 278; 128/750; 200/DIG. 2, 81 H, 81 R

[56] References Cited

U.S. PATENT DOCUMENTS

| | | | |
|---|---|---|---|
| 1,198,742 | 9/1916 | Meinecke | 604/174 |
| 1,710,701 | 4/1929 | Hertzberg | 604/41 |
| 1,853,202 | 4/1932 | Catlin | 604/32 |
| 2,420,507 | 5/1947 | Stratton | 604/34 |
| 2,458,419 | 1/1949 | McCormick | 604/33 |
| 2,838,629 | 6/1958 | Danzenhagen | 200/81 H |
| 3,042,039 | 7/1962 | Dahlstrom | 604/30 |
| 3,142,298 | 7/1964 | Koski et al. | 604/31 |
| 3,329,147 | 7/1967 | Barron | 604/34 |
| 3,750,668 | 8/1973 | Perl | 604/34 |
| 4,190,059 | 2/1980 | Holt | 604/27 |
| 4,413,214 | 11/1983 | Brown | 200/81 H |
| 4,682,979 | 7/1987 | Girouard | 604/118 |

Primary Examiner—C. Fred Rosenbaum
Assistant Examiner—Mario Costantino
Attorney, Agent, or Firm—Hurt, Richardson, Garner, Todd & Cadenhead

[57] ABSTRACT

An apparatus and method for providing a colonic lavage to a patient comprises a speculum for insertion into the colon of the patient with the speculum being generally tubular and having a tapered end within the colon with opposing openings formed therein and discharge and inlet openings outside the anal canal. The inlet opening is connected to a lavage liquid holding chamber through an inlet conduit and the discharge conduit is connected to a collection chamber through a discharge conduit. The discharge conduit has a resilient collapsible portion that passes through a pinch valve that can be actuated to close the discharge conduit. In operation, lavage liquid is pumped from the holding chamber while the pinch valve is closed causing the colon to fill with liquid. When the colon is full, pumping is discontinued and the pinch valve opened allowing liquid and loosened fecal matter within the colon to be purged through the discharge conduit to the collection chamber.

12 Claims, 4 Drawing Sheets

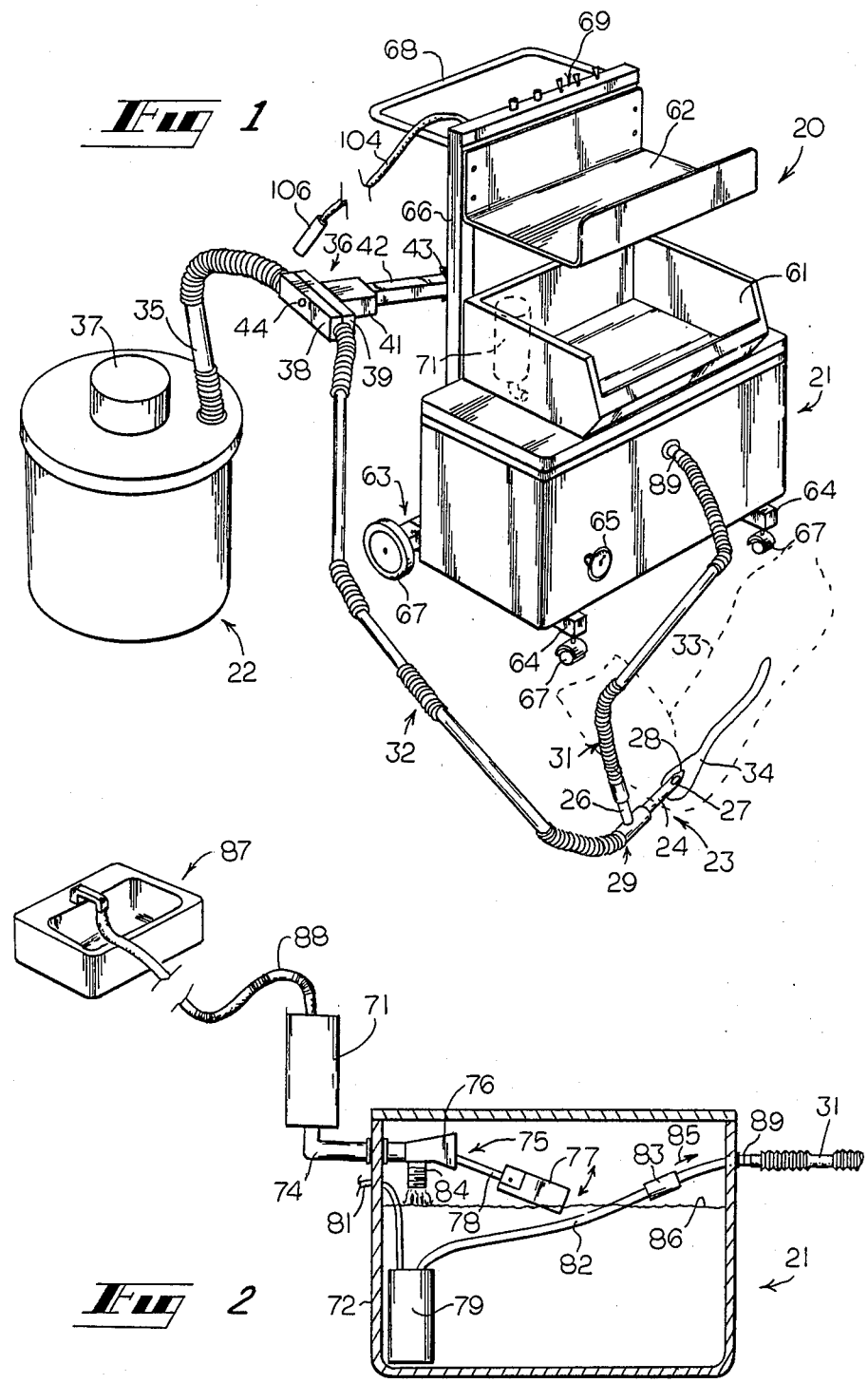

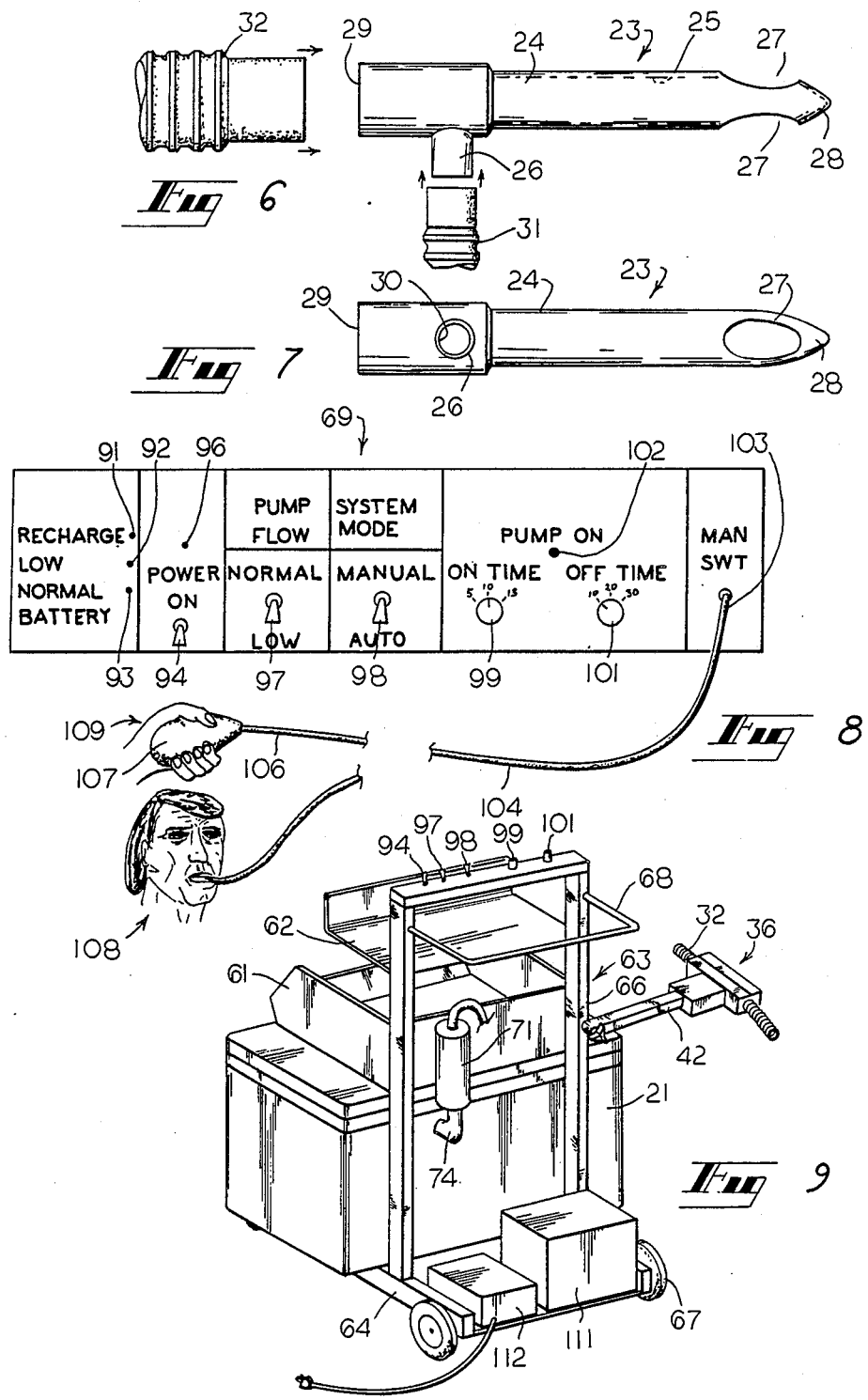

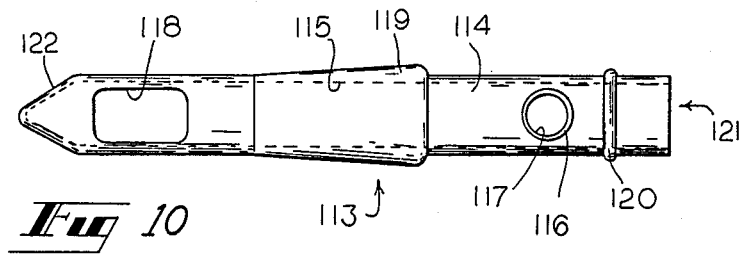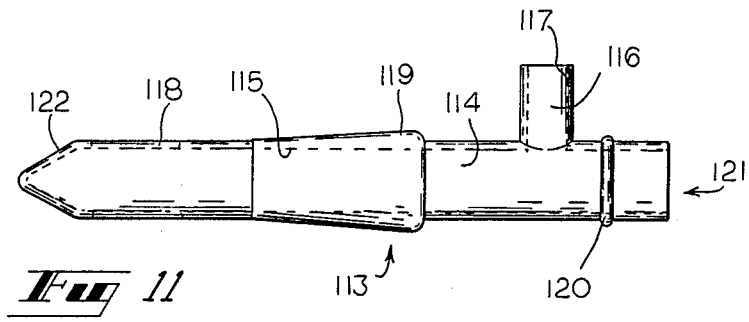

COLON HYDROTHERAPY AND EVACUATOR SYSTEM

REFERENCE TO RELATED APPLICATION

This application is a continuation-in-part of application Ser. No. 889,228 filed July 25, 1986 now abandoned.

FIELD OF THE INVENTION

This invention relates generally to a method and apparatus for providing a colonic lavage and particularly to a colon hydrotherapy and evacuator system suitable for use by a patient who is either having difficulty with bowel movements or has no ability at all for bowel evacuation

BACKGROUND OF THE INVENTION

Many people, particularly those who are elderly or handicapped, have substantial difficulty with bowel movements or have no ability at all to voluntarily evacuate their bowels. These people often require daily enemas and in some cases manual removal of fecal matter or even a colostomy becomes necessary. The use of conventional devices for administering enemas is inconvenient and uncomfortable for the patient, inefficient in the removal of fecal matter, and often unsanitary.

Colonic irrigation devices have been developed but have not proven to be entirely successful. Some of the prior art devices are expensive, bulky, difficult to operate and require that the patient be brought to the apparatus for treatment. The patient insertion nozzles or specula of the prior art devices are uncomfortable, often unsanitary and do not produce the motions of the lavage liquid within the colon necessary to loosen, break up and purge the fecal matter in the most efficient manner. While the patient can manually operate a few of the prior art devices with difficulty, most require operation by an attendant and in cases of incapacitated patients, the constant attention of an attendant is always required. In addition, since the attendant can not always judge when the proper amount of lavage liquid has been introduced into the patient, the patients colon is often not sufficiently cleaned.

Examples of some prior art irrigation devices are illustrated in U.S. Pat. Nos. 1,317,851 of Arnett, 2,027,588 of Hannon, 3,042,039 of Dahlstrom, and 3,771,522 of Waysilk, and 4,262,239 of Ardizzone.

SUMMARY OF THE INVENTION

Briefly described, the present invention is a colon hydrotherapy and evacuator system which includes a disposable patient insertion nozzle or speculum comprising an elongated one piece tubular body having a generally converging end for insertion into a patient's colon and an open discharge end which remains outside of the patient. A large, single longitudinal liquid passageway extends directly from the open discharge end to the converging end of the speculum and a pair of opposing nozzle openings are formed in the side of the speculum adjacent its converging end. A tubular liquid supply port defines an inlet opening that communicates with the liquid passageway adjacent the open discharge end of the speculum. The liquid supply port extends transversely from the body of the speculum adjacent the discharge end and is radially aligned with the opposed nozzle openings. A disposable, transparent discharge conduit extends from the discharge opening, through a pinch valve, and to a collection chamber. The pinch valve is adapted to collapse and release a portion of the discharge conduit closing and opening communication therethrough. The system also includes both manual and automatic control means and is mounted on a wheeled frame for portability.

In use, the speculum is inserted into the colon of a patient with the nozzle openings aligned with the widest portion of the colon. The pinch valve is actuated closing communication through the discharge conduit and lavage liquid is pumped from a liquid holding chamber through a disposable supply conduit to the inner opening of the speculum. Oxygenated air and lavage liquid are thus forced into the colon breaking up fecal matter therein. After a predetermined length of time, pumping is discontinued and the discharge conduit opened allowing lavage liquid and fecal matter to flow from the colon to the collection chamber.

Thus, it is an object of this invention to provide a colon hydrotherapy and evacuation system that is portable and that can be conveniently operated by an attendant or by the patient himself or that can operate automatically with predetermined timed cycles eliminating the need for the constant attention of an attendant even in cases of totally incapacitated patients.

Another object of the invention is to provide a colon hydrotherapy and evacuation system that exposes the colon to fresh oxygenated air and that forces lavage liquid laterally into the colon toward the hips of a patient where the colon is widest.

Still another object of the invention is to provide a colon hydrotherapy and evacuation system having a speculum with a single passageway and that has the capability of producing surges of lavage liquid at the nozzle openings of the speculum causing fecal matter to be broken up so that it can be purged from the colon.

A further object of the invention is to provide a colon hydrotherapy and evacuation system in which the parts that come into contact with the fecal matter of the patient are discarded after use eliminating the possibility of contamination remaining with the system.

Other objects, features and advantages of the invention will become apparent upon reading the following specification, when taken in conjunction with the accompanying drawings.

BRIEF DESCRIPTION OF THE DRAWINGS

FIG. 1 is a perspective illustration of the colon hydrotherapy and evacuator system showing the liquid holding chamber, the collection chamber, and the speculum and disposable conduits, with the discharge conduit extending through the pinch valve.

FIG. 2 is a side cross sectional view of the liquid holding chamber showing how the chamber is filled with liquid.

FIG. 6 is a plan view of the speculum showing the alignment of the nozzle openings and the liquid supply port and indicating the connection of the supply and discharge conduits.

FIG. 7 shows the speculum rotated ninety degrees from the view of FIG. 6.

FIG. 8 is a plan view of the control panel showing the alternate embodiments of the means for providing air pressure to the pressure sensitive remote switch.

FIG. 9 is a perspective view of the back of the system showing the battery, battery charger, and lavage liquid filter.

FIG. 10 shows an alternate embodiment of the speculum.

FIG. 11 shows the alternate embodiment of the speculum rotated ninety degrees from the view of FIG. 9.

DETAILED DESCRIPTION

Figure 3:
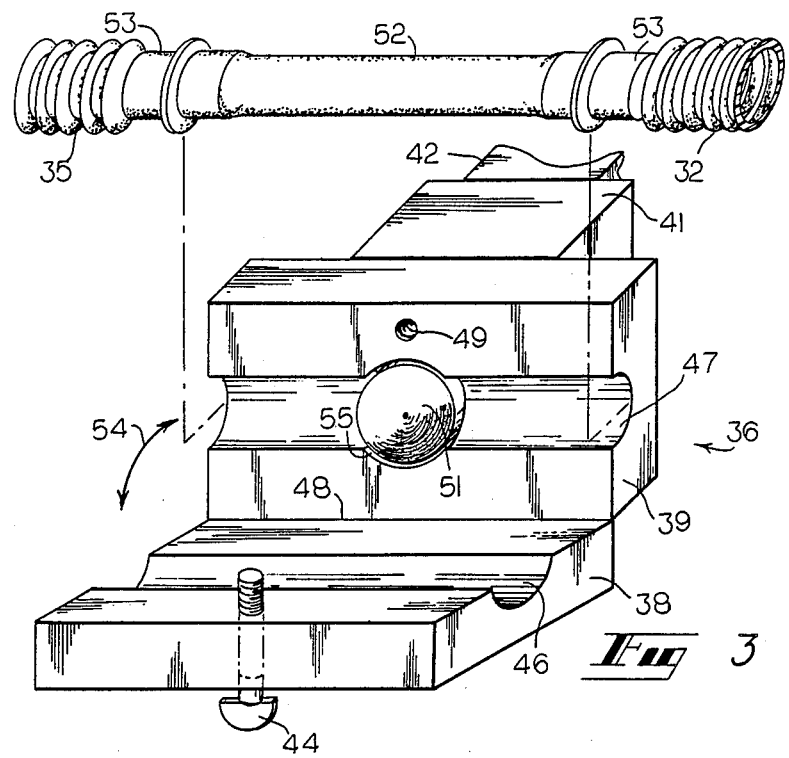
FIG. 3 is a perspective view of the pinch valve in its open configuration showing the pinch element and the placement of the resilient collapsible portion of the discharge conduit.

Referring now in more detail to the drawings, in which like numerals indicate like parts throughout all the views, FIG. 1 illustrates the colon hydrotherapy and evacuator system 20 which includes a liquid holding chamber 21 and a collection chamber 22. Patient insertion nozzle or speculum 23 having a tubular body 24 nozzle openings 27, supply opening 26, and discharge opening 29 is shown inserted into the colon 34 of a patient 33. The supply port 26 defining inlet opening 30 is connected through a flexible supply conduit 31 to the outlet port 89 of the liquid holding chamber 21. The outlet port 89 is in communication within the chamber (FIG. 2) with a pump 79 that can be actuated to pump liquid from the chamber 21 to the speculum 24.

Figure 4:
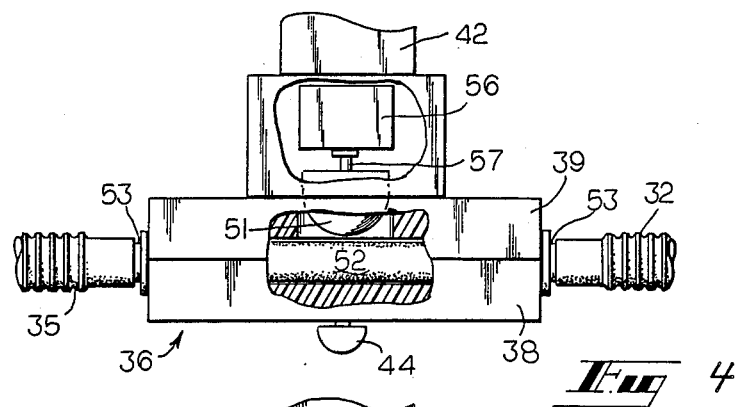
FIG. 4 is a side view partially in cross section of the pinch valve in its closed configuration with the pinch element retracted.
Figure 5:
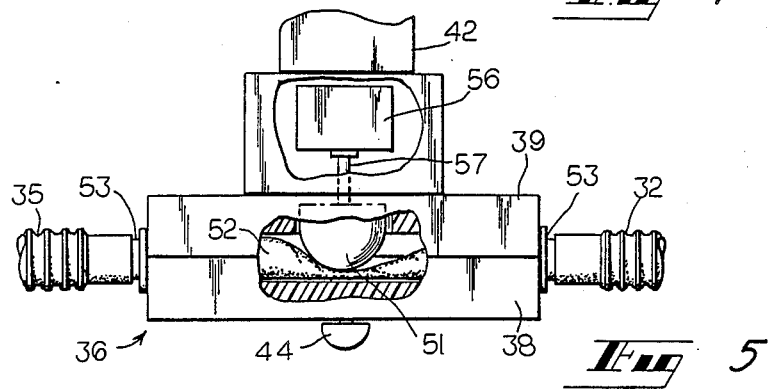
FIG. 5 is a side view partially in cross section of the pinch valve in its closed configuration with the pinch element extended against the collapsible portion of the discharge conduit.

The discharge opening 29 of the speculum 23 is in communication with the collection chamber 22 through a disposable transparent discharge conduit 32. The discharge conduit 32 has a resilient collapsible portion 52 as seen in FIGS. 3 through 5. The collapsible portion passes through a pinch valve 36 which clamps the collapsible portion of the discharge conduit in response to being actuated, preventing the flow of material from the speculum 23 to the collection chamber 22.

A stand 63 for supporting the liquid holding chamber 21 includes lower horizontal support members 64 and vertical stanchions 66. The pinch valve support arm 42 is rotatably connected to one of the stanchions 66 so that it can be pivoted up or down to an out-of-the-way position when not in use. The stand 63 is provided with a handle 68 and wheels 67 so that the system can be rolled from place to place. The control panel 69 (to be described later) is supported between the stanchions adjacent their upper ends. Additionally, FIG. 1 shows a thermometer 65 for indicating the temperature of the liquid within the holding chamber and a filter 37 connected to the collection chamber through which air within the chamber can escape as the chamber if filled.

FIG. 2 is a partial cross sectional view of the liquid holding chamber showing the internal parts thereof. It is seen to contain a pump 79 which is connected through a tube 82 to the outlet port 89 which is in communication with the liquid supply conduit 31. Check valve 83 is located in the tube and is arranged to allow the flow of liquid in the direction indicated by arrow 85 but prevents the flow of liquid in the opposite direction. The pump 79 is electrically coupled to the control circuit through wire 81. Float valve assembly 75 is connected through supply pipe 74, filter 71 and supply hose 88 to a conventional water faucet 87. Float valve assembly 75 has a spigot 84 and a valve portion 76 which is connected via connecting rod 78 to a float 77. With this arrangement, when liquid is moved from the water faucet 87 through the hose 88, the filter 71, and the pipe 74 to the float valve assembly 75, liquid will move through the float valve assembly 75 and out the spigot 84 until the level of the liquid within the container 21 lifts the float 77 causing the lever 78 to pivot, thus closing the valve 76 and terminating the movement of liquid into the container 21. The container 21 is provided with a lid 73 which fits securely on top of the container.

FIGS. 3, 4, and 5 show the pinch valve assembly 36. It is comprised generally of a front portion 38 and a rear portion 39 hingedly connected together along an edge 48. The front portion 38 has a hemicylindrical groove 46 formed therein and the rear portion 39 has an opposing hemicylindrical groove 47. The grooves are positioned so that when the front and rear portions are hinged together so that they are contiguous, the hemicylindrical grooves define a cylindrical cavity through the contiguous portions. A thumb screw 44 extends through the front portion 38 and into the threaded receiving hole 49 in the rear portion 39 so that the portions can be hinged together and securely held by the screw in their closed configuration.

A pinch element receiving hole 55 extends through the rear portion 39 and laterally intersects the groove 47. A pinch element or plunger 51 extends through the hole 55 and is attached through an attachment rod 57 to a solenoid 56. The solenoid 56 is in turn connected electrically to the control panel 69 from which it can be actuated as described below. The cylindrical cavity defined by the grooves 46 and 47 when the front and rear portions 38 and 39 are closed is adapted to receive the resilient collapsible portion 52 of the discharge conduit 32 as seen in FIG. 3. The collapsible portion 52 can be attached to the discharge conduit 32 via an adapter 53. In addition, a discharge conduit 35 can be attached to the other end of the flexible portion 52 and extended to a collection chamber. When the collapsible portion 52 is within the cavity with the front and rear portions 38 and 39 closed as seen in FIGS. 4 and 5, the solenoid 56 can be actuated causing the pinch element 51 to plunge forward collapsing the collapsible portion 52 against the wall of the groove 46 as best seen in FIG. 5. This action has the effect of preventing the flow of material through discharge conduit 32. When the solenoid 56 is deactuated as shown in FIG. 4, the pinch element 51 is retracted from the resilient collapsible portion 52 which allows material to pass from the discharge conduit 32 through the collapsible portion 52 and to a collection chamber through the discharge conduit 35.

FIGS. 6 and 7 show the speculum 23 which is disposable and formed from an inexpensive plastic or like material. The speculum 23 comprises an elongated tubular body 24 defining a longitudinal passageway 25 therethrough. One end of the speculum converges inwardly forming sloped side walls 28 in which a pair of opposed nozzle openings 27 are formed. The other end of the elongated tube is open forming a discharge opening 29. A transversely extending liquid supply port 26 defining an inlet opening 30 is attached to the elongated tube adjacent the discharge opening 29 so that the inlet opening 30 is in communication with the passageway 25. The liquid supply port 26 is or can be connected to liquid inlet conduit 31 and the discharge opening 29 can be connected to the discharge conduit 32 as shown in FIG.

6. It will be noted that liquid supply port 26 is radially aligned with the nozzle openings 27.

FIG. 9 is a rear perspective of the colon hydrotherapy and evacuation system showing the liquid inlet filter 71 and the inlet pipe 74. Also shown is the battery 111 which supplies power to the system and a battery charger 112 with which the battery can be charged by plugging the charger into a conventional wall outlet.

FIG. 8 shows the control panel of the system. It has battery indicator lights 91, 92, and 93 which display the status of the battery 111. Power switch 94 completes the circuit between the battery and the system when placed in its on position. Indicator light 96 is provided as a visual indication of whether the system power is on or off. Switch 97 is provided for controlling the rate of flow of liquid through the liquid supply conduit 31 to the speculum 23 by varying the rate at which the pump operates.

The system has a manual and an automatic mode of operation. The desired mode can be chosen using switch 98. In the automatic mode, the pump and pinch valve are automatically cycled on and off. The length of time that the pump is on and the valve closed which results in filling the patient's colon with liquid is controlled by potentiometer 99. The length of time that the pump is off and the pinch valve opened which results in allowing liquid to be drained from the colon through the discharge conduit is controlled by potentiometer 101. Thus, when switch 98 is in the automatic position, the system automatically cycles on and off for the times indicated by potentiometers 99 and 101. The pump also can be turned on at any time by depressing switch 102 and turned off by releasing the switch 102.

When the switch 98 is in the manual position, the activation of the pump and pinch valve is not cycled automatically but rather is controlled by an operator via the remote pressure switch hose 104. The system contains a pressure activated switch (not shown) that is connected to one end of the pressure hose 104. The pump is actuated and the pinch valve closed by creating excess pressure within the hose 104 which closes the pressure activated switch. The pump can be deactivated and the pinch valve opened when the excess pressure within the hose 104 is released. The excess pressure within the hose is created by an operator of the system by blowing into a mouth piece 106 connected to the hose 104 or alternately by depressing a squeeze bulb 107 that can be connected to the hose 104. In this way, an operator or the patient himself can manually determine how long the pump should remain actuated filling the colon and how long the pump should remain inactive allowing the colon to be drained.

FIGS. 10 and 11 show an alternate embodiment of the speculum 113 having a generally tubular body 114 defining a single longitudinal passageway 115 therethrough. The speculum 113 has a generally tapered end 122 for insertion into the colon of a patient and an open discharge end 121. A pair of opposing, generally rectangular nozzle openings 118 are formed in the speculum body adjacent the tapered end 122 and a generally tubular inlet port 116 extends transversely from the body 114 adjacent the discharge end 121. The inlet port 116 defines an inlet opening 117 that is in communication with the liquid passageway 115. An annular flange 120 extends around the periphery of the speculum adjacent its discharge end for forming a tight fit with the discharge conduit (not shown). An annular tapered retaining collar 119 is formed in the body 114 and near the middle portion thereof. The collar 119 extends generally outwardly around the body 114 and serves to help maintain the speculum inside the colon as described below.

OPERATION

When using the system of FIGS. 1 through 9 to provide a colonic lavage to a patient, the liquid holding chamber 21 is filled with lavage liquid by connecting the hose 88 to a source of lavage liquid which can be a conventional sink faucet. The faucet can be adjusted in the conventional manner to provide water at a temperature that is comfortable to the patient. The temperature of the lavage liquid within the holding chamber is indicated by thermometer 65. Water flows from the faucet 87 through hose 88 and through filter 71 and into the liquid holding chamber 21 through pipe 74 and float valve assembly 75. The filter 71 is of a standard charcoal construction which removes chlorine and other harmful chemicals from the water.

As the liquid holding chamber fills with water, float 77 is raised by the water causing arm 78 to pivot which closes the valve 76 stopping the flow of liquid into the container. The faucet then is turned off and the hose 88 disconnected from the system so that the system can be moved to the vicinity of a patient to be treated.

The filled holding chamber 21 is then rolled via stand 63 to a patient who is preferably lying in a reclined position on a bed. A package containing the speculum 23 and the disposable supply and discharge conduits 31, 32, and 35 as well as rubber gloves and lubricating jelly is taken from chamber 21 and the elements therein removed. Supply conduit 31 is attached at one end to the supply inlet 26 of the speculum 23 and connected at its other end to the supply port 89 on the liquid holding chamber 21. Discharge conduit 32 is connected at one end to the discharge opening 29 of the speculum 23 and at its other end to one end of the collapsible conduit 52 which extends through the pinch valve. The other end of the flexible conduit is connected to one end of a discharge conduit 35 and the other end of the conduit 35 is connected to the collection chamber 22 which preferably remains in the patients room.

The speculum 23 is placed through the anal canal and into the colon of the patient which has a generally elliptical cross section being wider in a direction aligned with the hips. The opposed nozzle openings can be oriented so that lavage liquid enters the colon in the direction of its widest extent by aligning the inlet opening, which in turn aligned with the inner openings, with the hips of the patient. If the patient is lying on his back, the supply conduit 31 will lie naturally across the top of the bed which insures that the liquid supply inlet 26 and consequently the aligned inner openings 27 within the colon of the patient are oriented generally parallel to the patients hips. The support arm can then be rotatably adjusted so that the pinch valve 36 is approximately even with the top surface of the bed. When using the embodiment of the speculum shown in FIGS. 10 and 11, the body 114 of the speculum 113 is inserted through the anal canal such that the annular collar 119 is just inside the canal opening. In this way, the resilient tissue and muscles of the anus cause the anal canal to tend to close behind the collar 119 securely maintaining the speculum within the anal canal and colon of the patient.

With the system thus in place, the pump 79 is actuated and the responsive pinch valve 36 closed either by the automatic timing circuit or by the patient or attendant using the remote manual pressure tube. This causes water to be pumped from the holding chamber 21 through the supply conduit 31 and to the speculum 23. Initially, if the air has not been flushed from the conduits, the portion of the discharge conduit between the closed pinch valve and the speculum will fill with lavage liquid forcing the air trapped therein into the colon of the patient. This exposes the tissue of the colon to fresh oxygenated air and kills certain harmful bacteria within the colon. When the discharge conduit 32 has been filled, lavage liquid will begin to flow into the colon of the patient as shown in FIG. 1. Because of the generally horizontal orientation of the inner openings, the lavage liquid flows laterally toward the hips of the patient where the colon is widest and not flattened by the weight of the patient.

At the end of the predetermined cycle in the automatic mode or upon release of pressure within tube 104 in the manual mode, the pump 79 will be deactuated. The pinch valve can be simultaneously opened to provide immediate discharge or can be left closed for a predetermined length of time holding the lavage liquid within the colon before it is discharged. When the pinch valve is opened, lavage liquid and loosened fecal matter within the colon flow through nozzle openings 27 and through the discharge conduit to the collection chamber 22. Contaminated lavage liquid is prevented from flowing through the supply conduit 31 back to the liquid holding chamber by the one way check valve 83. As liquid fills the collection chamber, air within the chamber escapes through charcoal filter 37 at the top of the chamber which removes odor and bacteria from the escaping air.

A distinct advantage of the single passageway speculum is that in cases where the fecal matter is too large to pass through the nozzle openings of the speculum, the patient or attendant can actuate and deactuate the pump and pinch valve a few times in rapid succession which creates alternating surges of lavage liquid at the inner openings. This tends to break up the fecal matter so that it will fit through the nozzle openings and can be purged from the colon. This jogging action is not possible with prior art specula having two passageways because liquid always flows out through the discharge passage and can not be surged in and out to break up fecal matter that can be clogging the system. Also, the large single longitudinal passageway 25 extending from nozzle openings 27 to discharge opening 29 of the speculum assures that the maximum diameter passage is formed for the fecal matter.

When the patients colon has been thoroughly cleaned, the speculum 23 is removed, supply conduit 31 is disconnected from the holding chamber 21, discharge conduit 32 is disconnected from flexible conduit 52 and discharge conduit 35 is disconnected from flexible conduit 52 and from the collection chamber. The speculum, supply conduit and discharge conduits are then discarded. The flexible conduit 52 can also be discarded if desired but is designed to be used several times before being replaced.

It should be understood that the embodiments of the invention described herein merely illustrated principles of the invention in a preferred form. Other modifications and variations can be made thereto without departing from the spirit and scope of the invention as set forth in the claims.

I claim:

1. An apparatus for providing a colonic lavage to a patient comprising:
    a container for receiving and holding a lavage liquid;
    a speculum for insertion through the anal canal and into the colon of the patient, said speculum defining a longitudinal passage therethrough and having a nozzle opening for placement within the colon, a discharge opening for placement outside the anal canal, and a liquid inlet opening for placement outside the anal canal;
    a liquid delivery conduit in communication at one of its ends with said container and in communication at its other end with said liquid inlet opening;
    a pump means disposed within said container for delivering lavage liquid under pressure from said container through said liquid delivery conduit to said liquid inlet opening of said speculum;
    a collection chamber for receiving contaminated lavage liquid;
    a filter disposed on the top of said collection chamber for removing odor and bacteria from the air within said chamber as the chamber fills with contaminated lavage liquid;
    a discharge conduit having a resilient collapsible portion, said discharge conduit being in communication at one of its ends with said discharge opening and in communication at its other end with said collection chamber;
    means for selectively closing and opening said discharge conduit, said means comprising a pinch valve for selectively collapsing and releasing the resilient collapsible portion of the discharge conduit;
    means for creating a pulsing action of lavage liquid through said inner opening of said speculum comprising means for alternately actuating said pump means while simultaneously closing said discharge conduit and deactuating said pump means while simultaneously opening said discharge conduit.

2. The apparatus of claim 1 wherein said speculum comprises an elongated tubular body defining a longitudinal passage and having a first generally tapered end for insertion into the anal canal, a second open end for connection to said discharge conduit and a tubular transversely extending inlet opening in communication with said longitudinal passage adjacent said open end, said tapered end having a pair of opposing openings formed therein for the movement of lavage liquid into the colon and movement of liquid and fecal matter out of the colon.

3. The apparatus of claim 2 wherein said inlet opening is radially aligned on said body with said opposing openings whereby said speculum can be inserted into a colon having a generally elliptical cross section and said opposing openings aligned with the semi-major axis of the ellipse within the colon by aligning said inlet opening with the axis.

4. The apparatus of claim 1 wherein said means for alternately actuating said pump means while closing said discharge conduit and deactuating said pump means while opening said discharge conduit comprises a control means including a plurality of timing means, said control means being operatively connected to said pump means and said pinch valve for selectively actuating and deactuating said pump means and said pinch valve in response to signals from said plurality of timing means.

5. The apparatus of claim 1 wherein said means for alternately actuating said pump means while closing said discharge conduit and deactuating said pump means while opening said discharge conduit comprises a control means being operatively connected to said pump means and said pinch valve for selectively actuating and deactuating said pump means and said pinch valve in response to said manual switch being activated and deactivated.

6. The apparatus of claim 5 wherein said switch is activated by excess air pressure and wherein said control means includes a remote pressure tube operatively attached to said switch at one end and having means for producing excess air pressure within said tube attached to its other end.

7. The apparatus of claim 6 wherein said means for producing excess air pressure within said tube comprises a mouthpiece adapted to be placed into and receive air pressure from the mouth of an operator.

8. The apparatus of claim 6 wherein said means for producing excess air pressure within said tube comprises a squeeze bulb adapted to be squeezed by an operator.

9. The apparatus of claim 1 further comprising means for permitting the flow of liquid in a direction from said container to said speculum and preventing the flow of liquid in a direction from said speculum to said container, said means comprising a one-way valve in series with said liquid delivery conduit between said pump and said speculum.

10. The apparatus of claim 1 further comprising means for moving the apparatus from place to place, said means comprising a stand having a generally horizontal support surface, a plurality of wheels attached to the bottom of the support surface and a pair of vertical stanchions extending upwardly from the support surface with the upper ends of said stanchions having a handle for pushing the stand across the floor.

11. The apparatus of claim 10 further comprising a pinch valve support arm rotatably attached at one end to one of said stanchions and having said pinch valve firmly attached to its other end and means for releasibly maintaining said support arm in a predetermined rotary attitude with respect to said stanchion.

12. A method for clearing a blockage from a speculum of the type having a tubular body defining a single longitudinal passageway therethrough, a tapered end with opposing nozzle openings in communication with said passageway for insertion into the colon of a patient and a discharge end having discharge and liquid inlet openings in communication with said passageway for positioning outside the anal canal comprising the steps of:

selecting a flow rate for moving liquid through the liquid inlet opening;

moving liquid through the liquid inlet opening while preventing the flow of liquid through the discharge opening;

discontinuing the movement of liquid through the liquid inlet opening while allowing the flow of liquid through the discharge opening; and repeating the steps of moving liquid through the liquid inlet opening and discontinuing the movement of liquid through the liquid inlet opening in a rapid, alternating manner to generate a pulsating flow of liquid through the nozzle openings to break up the blocking material so that it can flow through said longitudinal passageway and out the discharge opening.

* * * * *